United States Patent [19]
Fernandez Puentes et al.

[11] Patent Number: 5,852,033
[45] Date of Patent: Dec. 22, 1998

[54] METHODS OF TREATMENT USING LAMELLARIN-CLASS ALKALOIDS

[75] Inventors: Jose Luis Fernandez Puentes, Leon; Dolores Garcia Gravalos, Madrid; Ana Rodriguez Quesada, Malaga, all of Spain

[73] Assignee: Pharma Mar, s.a., Madrid, Spain

[21] Appl. No.: 496,465

[22] Filed: Jun. 29, 1995

[51] Int. Cl.$^6$ .................................................. A61K 31/44
[52] U.S. Cl. ............................................................ 514/283
[58] Field of Search ............................................. 514/283

[56] References Cited

PUBLICATIONS

Higgins, C.F. The multidrug resistance P–glycoprotein, *Curr. Opin. Cell Biol.* 5:684–687, 1993.
Nooter, K. et al., Multidrug resistance (mdr) genes in human cancer. *Br. J. Cancer* 63:663–9, 1991.
Arceci, R.J., Clinical significance of P–glycoprotein in multidrug resistance malignancies, *Blood*, 81:2215–2222, 1993.
Benchimol, S., et al., P–glycoprotein and tumor progression, *J. Natl. Cancer Inst.* 86:814–815, 1994.
Tsuruo, T., et al., Overcoming of vincristine resistance in P388 leukemia in vivo and in vitro through enhanced cytotoxicity of vincristine and vinblastine by verapamil. *Cancer Res.* 41:1967–72, 1981.
Deuchars, K., et al., P–glycoprotein and multidrug resistance in cancer therapy. *Seminars in Oncology*, 16:156–165, 1989.
Gottesman, M.M., et al., Biochemistry of multidrug resistance by the multidrug transporter. *Annu. Rev. Biochem.*, 62:385–427, 1993.
Beck, W.T., et al., Photoaffinity substrates for P–glycoprotein. *Biochem. Pharmacol*, 43:89–93, 1992.
Ozols, R.F., et al., Verapamil and adriamycin in the treatment of drug resistant ovarian cancer patients. *J. Clin. Oncol.*, 5:541–547, 1987.
Andersen, R.J., et al., Metabolites of the marine posobranch mollusc, *Lamellaria sp. J. Am. Chem. Soc.*, 107:5492–5495, 1985.
Linquist, N., et al., New alkaloids of the lamellarin class from the marine ascidian, *Didemaun Chartacum* (Sluiter, 1909), *J. Org. Chem.* 53:4570–4574, 1988.
Carroll, A.R., et al., Studies of australians ascidians. I. Six new lamellarin class alkaloids from a colonial ascidian, *Didemnum, sp. Aust. J. Chem.* 46:489–51, 1993
Mosmann, T. Rapid coorimetric assay for the cellular growth and survival; application to proliferation and cytoxicity assays. *Journal of Immunological Methods*, 65:55–63, 1983.

*Primary Examiner*—Jerome D. Goldberg
*Attorney, Agent, or Firm*—Ernest V. Linek; Dike, Bronstein, Roberts & Cushman LLP

[57] ABSTRACT

The lamellarin compounds disclosed herein have been found to be inhibitors of MDR, i.e., acquired multidrug resistance, which has become a major problem in the treatment of various cancers. The lamellarin compounds disclosed herein have also been found to be cytotoxic to MDR cells. MDR is believed to be associated with certain alterations in tumor cells, including an over-expression of a certain high molecular weight membrane glycoprotein and a decrease in the ability of the tumor cell to accumulate and retain chemotherapeutic agents. The present invention is thus directed to methods of treating MDR-type tumors with an effective anti-MDR amount (either inhibitory or cytotoxic) of one or more lamellarin compounds, which compounds have been found to be effective antitumoral agents against MDR cells.

15 Claims, No Drawings

METHODS OF TREATMENT USING LAMELLARIN-CLASS ALKALOIDS

BACKGROUND OF THE INVENTION

Marine ascidians have proven to be rich sources of structurally diverse alkaloids, many of which exhibit a broad spectrum of biological activity. Members from the family Didemnidae are generally highly colored, encrusting organisms, colonial by habit, and characteristically contain chemical constituents which are derived from amino acids. The polyaromatic lamellarin alkaloids, for example, are probably derived from three tyrosine residues. The lamellarin skeleton was first identified in an isolate from a prosobranch mollusc, *Lamellaria sp.*, from Palau, but has more recently been found in the didemnid ascidian *Didemnum chartaceum* from the Seychelles. It has also been suggested that the lamellarins may be distantly related to the tunichromes, reducing blood pigments isolated from the ascidian *Ascidia nigra*.

Anderson et al., *J. Am. Chem. Soc.*, 107: 5492–5495 (1985), describe the isolation and characterization of four polyaromatic metabolites, the lamellarins A–D, obtained from a marine prosobranch mollusc, *Lamellaria sp.* The structure of lamellarin A was determined by an X-ray crystallographic study and the structures of lamellarins B–D were assigned by interpretation of spectral data. The disclosure of this publication is hereby incorporated herein by reference.

Lindquist et al., *J. Org. Chem.*, 53: 4570–4574 (1988) describes the isolation and characterization of four new alkaloids of the lamellarin class from the marine ascidian *Didemnum chartaceum* obtained from the Indian Ocean. The structure of lamellarin E was determined by spectroscopic and X-ray crystallographic methods. The structure of lamellarins F–H were elucidated by interpretation of NMR spectral data. The disclosure of this publication is hereby incorporated herein by reference.

Carroll et al., *Aust. J. Chem.*, 46: 489–501 (1993) describes six new polyaromatic alkaloids, the lamellarins I, J, K, L, M and the triacetate of lamellarin N, and four known alkaloids of this type, lamellarin A, B, C and the triacetate of lamellarin D, isolated from a marine ascidian *Didemnum sp.* The disclosure of this publication is hereby incorporated herein by reference.

The lamellarin compounds disclosed herein have been found to be non-toxic inhibitors of acquired multidrug resistance (MDR), which has become a major problem in the treatment of various human tumors. The lamellarin compounds have also been found to be cytotoxic to MDR cells. Both of these activities are useful in the treatment of MDR tumors.

Drugs of proven antitumor chemotherapeutic value to which multidrug resistance has been observed include vinblastine, vincristine, etoposide, teniposide, doxorubicin (adriamycin), daunorubicin, plicamycin (mithramycin) and actinomycin D. Many tumors are intrinsically multidrug resistant (e.g., adenocarcinomas of the colon and kidney) while other tumors acquire multidrug-resistance during therapy (e.g., neuroblastomas and childhood leukemias).

While not wishing to be bound by theory, it is believed that the mdr gene encodes a glycoprotein (P-170 or P-glycoprotein). This protein is though to act as an energy dependent efflux pump that is utilized in normal cells, as well as in cancer cells, for their detoxification. But, when the latter are able to over express the gene, the effect of an antitumor drug in such cells is highly reduced and therefore the MDR phenotype appears. See, for instance, Deuchars et al., *Seminars in Oncology*, 16: 156–165 (1989) and Gottesman et al., *Ann. Rev. Biochem.*, 62: 385–427 (1993). Two ways to overcome MDR are (1) find inhibitors of P-170 or (2) find drugs which are as active against the MDR cancer cell line as they are to said cell line's normal counterpart.

MDR inhibitors are agents that are used to restore drug sensitivity to some multidrug resistant tumor cells. Among the agents known to possess this property are certain calcium transport blockers (e.g., verapamil) and certain calmodulin inhibitors (e.g., trifluoperazine). However, clinical use of these compounds has been limited by their toxic side effects. See, Ozols et al., *J. Clin. Oncol.*, 5: 541–547 (1987); see also, Twentyman et al., *Int. J. Radiat. Oncol. Biol. Phys.*, 12: 1355 (1986). The minimization (or elimination) of such toxic side effects is thus an important factor in the selection of a MDR inhibitor.

Since verapamil was firstly described, several natural product compounds have been reported to overcome or inhibit MDR. Examples include the plant alkaloid thailblastine (see, Chen et al., *Cancer Res.*, 53: 2544–2547 (1993)), and the marine natural product patellaminde D (see, Williams et al., *Cancer Letters*, 71: 97–102 (1993)). Other examples of compounds active against MDR cells are the peptide cyclosporin A (see, Beck et al., *Biochem. Pharmacol.*, 43: 89–93 (1992)), a heterocyclic compound (5-N-acetylardeemin—see, Karwowsky et al., *J. Antibiotics*, 46: 374–379 (1993)), Geodiamolide A, jaspamide, and glaciasterol A (see, Stingi et al., *Cancer Chemother. Pharmacol.*, 30: 401–406 (1992)). Thus, the search for new MDR inhibitors and compounds active against MDR cells continues.

SUMMARY OF THE INVENTION

The lamellarin compounds disclosed herein have been found to be non-toxic inhibitors of acquired multidrug resistance (MDR), which has become a major problem in the treatment of various human tumors. The lamellarin compounds have also been found to be cytotoxic to MDR cells. Both of these activities are useful in the treatment of MDR tumors. As discussed above, MDR is believed to be associated with certain alterations in tumor cells, including an over-expression of a certain high molecular weight membrane glycoprotein and a decrease in the ability of the tumor cell to accumulate and retain chemotherapeutic agents.

The present invention is thus directed to methods of treating selected tumors with an effective anti-MDR amount, i.e., either an inhibitory amount, a cytotoxic amount, or both, of one or more lamellarin compounds, which compounds have been found to be effective antitumoral agents against MDR cells.

Thus, in one preferred embodiment of the present invention, there is provided a method of treating (i.e., by slowing the growth or arresting the growth) MDR tumors comprising administration of an effective MDR inhibitory amount of a compound having the one (or both) of the following formulae:

A 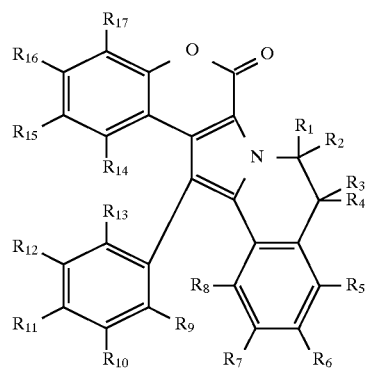

B 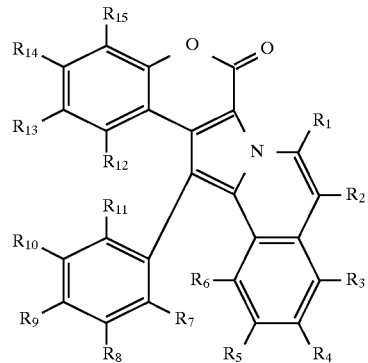

wherein $R_1$ to $R_{17}$ (in Formula A) or $R_1$ to $R_{15}$ (in Formula B) may be the same or may be different and are selected from the group consisting of —H, —OH, -Me, -Et, -Pro, —OMe, —COMe, and —OCOMe.

Thus, in another preferred embodiment of the present invention, there is provided a method of treating (i.e., by slowing the growth or stopping the growth) MDR tumors comprising administration of an effective MDR cell cytotoxic amount of an anti-MDR lamellarin compound, particularly of Formula A or B as shown above.

Thus, the present invention is directed to methods of treatment using the lamellarin compounds embraced in the two general Formulas A and B, and more particularly to methods of treatment utilizing the lamellarins shown below Table I as especially preferred examples of compounds useful in the presently claimed invention.

TABLE I

STRUCTURE OF KNOWN LAMELLARINS

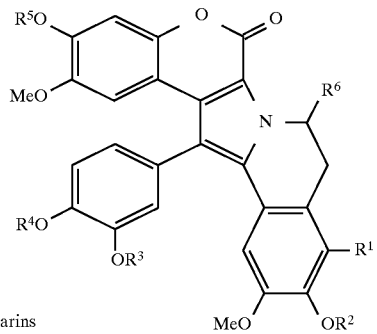

GROUP-I: Saturated Lamellarins

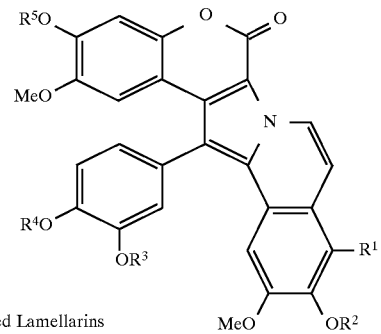

GROUP-II: Insaturated Lamellarins

| Lamellarin | $R^1$ | $R^2$ | $R^3$ | $R^4$ | $R^5$ | $R^6$ | Lamellarin | $R^1$ | $R^2$ | $R^3$ | $R^4$ | $R^5$ |
|---|---|---|---|---|---|---|---|---|---|---|---|---|
| A | OMe | Me | Me | H | H | OH | B | OMe | Me | Me | H | H |
| I | OMe | Me | Me | Me | H | H | D-triacetate | H | COMe | Me | COMe | COMe |
| I-acetate | OMe | Me | Me | Me | COMe | H | M | OH | Me | Me | H | H |
| I-methylate | OMe | Me | Me | Me | Me | H | M-triacetate | OCOMe | Me | Me | COMe | COMe |
| J | H | H | Me | Me | H | H | N-tricetate | H | COMe | COMe | Me | COMe |
| K | OH | Me | Me | H | H | H | | | | | | |
| K-triacetate | OCOMe | Me | Me | COMe | COMe | H | | | | | | |
| L | H | H | H | Me | H | H | | | | | | |
| L-triacetate | H | COMe | COMe | Me | COMe | H | | | | | | |

DETAILED DESCRIPTION OF THE PREFERRED EMBODIMENTS

As described above, the present invention is directed to novel methods of treating tumors in mammals, comprising administering to a patient in need of such treatment, lamellarins as either inhibitors of MDR activity, or as MDR cytotoxic compounds. Thus, the lamellarins may be employed either alone against MDR tumors, or in combination with other anti-tumor drugs, as effective treatments against MDR cells.

The present invention is also directed to pharmaceutical compositions comprising one or more lamellarin compounds useful as specified herein. Moreover, such pharmaceutical compositions can further comprise one or more other antitumor drug, particularly those in which multidrug resistance has been observed; including for example vinblastine, vincristine, etoposide, teniposide, doxorubicin (adriamycin), daunorubicin, plicamycin (mithramycin) and actinomycin D.

Thus, the present invention is also directed to a method of improving the antitumor chemotherapeutic effect of MDR affected drugs in patients in need of such treatment, comprising coadministering (simultaneously or sequentially) the MDR affected antitumor drug with an effective anti-MDR effective amount of a lamellarin compound.

As demonstrated herein, the compounds of the present invention have been found to possess MDR antitumor activity both in vitro and in vivo, and as such it is believed that these cytotoxic compounds will be useful as MDR antitumor compounds in animals and preferably in humans.

When being used as cytotoxic or antitumor inhibitory MDR agents, the compounds of the present invention can be prepared and administered in various dosage forms, especially parenteral dosage forms. It will be clear to those having ordinary skill in this art that the dosage forms may comprise as the active ingredient, one or more of the compounds of the present invention. The skilled artisan will likewise recognize that the dosages and routes of administration will vary according to the needs of the patient and the specific activity of the active ingredient(s). The determination of these parameters is within the ordinary skill of the practicing physician.

Tables II and III below provide additional data regarding the MDR inhibitory activity of the lamellarins. These data were generated by the procedures described below.

TABLE II

LAMELLARINS TOXICITY TO SENSITIVE AND RESISTANT TUMOR CELL LINES

ACTIVITY: $IC_{50}$ (μg/ml)

| LAMELL-ARIN | STAND-ARD | Mouse Limphoma | | Chinese Hamster Ovary | |
|---|---|---|---|---|---|
| | | P-388 | P-388/SCHABEL (MDR) | CHOB1 | CHOC5 (MDR) |
| A | | 0.5 | 0.5 | 0.2 | 0.4 |
| B | | 5.5 | 5.5 | 3.0 | 10.0 |
| D-triacetate | | 0.07 | 0.09 | 0.03 | 0.04 |
| I | | 2.5 | 2.5 | 0.2 | 1.0 |
| I-acetate | | 5.5 | 5.5 | 2.5 | 5.0 |
| I-methylate | | 2.5 | 3.0 | 0.5 | 2.5 |
| J | | 1.5 | 2.0 | 0.3 | 0.6 |
| K | | 0.1 | 0.1 | 0.1 | 0.4 |
| K-triacetate | | 0.06 | 0.1 | 0.1 | 0.1 |
| L | | 0.6 | 0.7 | 0.4 | 0.6 |
| L-triacetate | | 1.5 | 1.5 | 1.5 | 1.5 |
| M | | 0.08 | 0.09 | 0.04 | 0.09 |
| M-triaacetate | | 0.6 | 0.7 | 0.5 | 2.0 |
| N-triacetate | | 0.09 | 0.2 | 0.06 | 0.1 |
| | Adriamycin | 0.15 | 1.2 | 0.15 | 3.0 |
| | Verapamil | 10.0 | 10.0 | 9.0 | 4.0 |
| | PSC833 | 0.02 | 0.05 | 0.04 | 0.1 |

TABLE III

Adriamycin Toxicity to Resistant Cells (MDR) in Presence or in Absence of Reversing Agents (R.A.)
Gain of Sensitivity (G.S.) = $IC_{50}$ Control/$IC_{50}$ R.A.

| REVERSING AGENT (R.A.) | R.A. (μg/ml) | Mouse Limphoma (MDR) | | Chinese Hamster Ovary (MDR) | |
|---|---|---|---|---|---|
| | | P-388/SCHABEL $IC_{50}$ (μg/ml) | G.S. | CHOC5 $IC_{50}$ (μg/ml) | G.S. |
| CONTROL (Adriamycin only) | 0 | 1.2 | | 3.0 | |
| Verapamil | 1 | 0.15 | 8.0 | 0.2 | 15.0 |
| (Standard) | 3 | 0.06 | 20.0 | 0.1 | 30.0 |
| Lamellarin A | 0.1 | 0.7 | 1.7 | 2.0 | 1.5 |
| | 0.3 | 0.2 | 6.0 | 1.0 | 3.0 |
| Lamellarin B | 1 | 0.3 | 4.0 | 0.7 | 4.3 |
| | 3 | 0.15 | 8.0 | 0.003 | 1,000 |
| Lamellarin D-triacetate | 0.01 | 0.7 | 1.7 | 2.5 | 1.2 |
| | 0.03 | 0.12 | 10.0 | 0.003 | 1,000 |
| Lamellarin I | 0.1 | 0.4 | 3.0 | 0.6 | 5.0 |
| | 0.3 | 0.15 | 8.0 | 0.15 | 20.0 |
| | 1 | 0.04 | 30.0 | 0.01 | 300 |
| Lamellarin I-acetate | 1 | 0.25 | 4.8 | 0.4 | 7.5 |
| | 3 | 0.07 | 17.1 | 0.08 | 37.5 |
| Lamellarin I-Methylate | 0.3 | 0.2 | 6.0 | 0.4 | 7.5 |

TABLE III-continued

Adriamycin Toxicity to Resistant Cells (MDR) in Presence or in Absence of Reversing Agents (R.A.)
Gain of Sensitivity (G.S.) = $IC_{50}$ Control/$IC_{50}$ R.A.

| REVERSING AGENT (R.A.) | R.A. (µg/ml) | Mouse Limphoma (MDR) P-388/SCHABEL $IC_{50}$ (µg/ml) | G.S. | Chinese Hamster Ovary (MDR) CHOC5 $IC_{50}$ (µg/ml) | G.S. |
|---|---|---|---|---|---|
|  | 1 | 0.04 | 30.0 | 0.12 | 25.0 |
| Lamellarin J | 0.1 | 0.9 | 1.3 | 2.5 | 1.2 |
|  | 0.3 | 0.7 | 1.7 | 2.0 | 1.5 |
| Lamellarin K | 0.03 | 0.9 | 1.3 | 2.0 | 1.5 |
|  | 0.1 | 0.3 | 4.0 | 0.9 | 3.3 |
| Lamellarin K-triacetate | 0.03 | 0.4 | 3.0 | 1.0 | 3.0 |
| Lamellarin L | 0.1 | 0.4 | 3.0 | 2.5 | 1.2 |
|  | 0.3 | 0.003 | 400 | 2.0 | 1.5 |
| Lamellarin L-triacetate | 0.3 | 0.2 | 6.0 | 0.1 | 30.0 |
|  | 1 | <0.003 | >400 | 0.003 | 1,000 |
| Lamellarin M | 0.03 | 1.0 | 1.2 | 1.2 | 2.5 |
| Lamellarin M-triacetate | 0.1 | 0.6 | 2.0 | 2.0 | 1.5 |
|  | 0.3 | 0.4 | 3.0 | 1.0 | 3.0 |
| Lamellarin N-triacetate | 0.01 | 0.8 | 1.5 | 2.0 | 1.5 |
|  | 0.03 | 0.3 | 4.0 | 0.4 | 7.5 |

Determination of MDR Activity

Sensitive and MDR cells were maintained, in logarithmic phase of growth, in Eagle's Minimum Essential Medium, with Earle's Balanced Salts, with non-essential amino acids, with 2.0 mM L-glutamine, without sodium bicarbonate (EMEM/neaa), supplemented with 5% Fetal Calf Serum (FCS), $10^{-2}$M sodium bicarbonate and 0.1 g/l penicillin G+0.1 g/l streptomycin sulfate.

In Vitro cell cytotoxicity was determined using the 3-[4,5-dimethylthiazol-2-yl]-2,5-dipheniltetrazolium bromide (MTT), from Sigma Ref:M-2128, for quantitative measurement of cell growth and viability. See, T. Mosmann, "Rapid Colorimetric Assay for Cellular Growth and Survival: Application to Proliferation and Cytotoxicity Assays," *Journal of Immunological Methods*, 65: 55–63 (1983).

The tumor cell lines employed have been: P-388 (ATCC CCL 46), suspension culture of a lymphoid neoplasm from a DBA/2 mouse and its corresponding MDR cell line P-388/SCHABEL; CHOB1 (ATCC CCL 16), monolayer culture of chinese hamster ovary and its corresponding MDR cell line CHOC5. See, Rauscher III, et al., "Characterization of Auromycin-Resistant Hamster Cell Mutants that Display a Multidrug Resistance Phenotype," *Molecular Pharmacology*, 38: 198–206 (1990).

This form of assay employs 96-well cell culture plates 99 mm diameter. Cells were seeded into wells at $1 \times 10^3$ cells per well in 100 µl aliquots of EMEM 5% FCS containing different concentrations of the corresponding lamellarins and other compounds (standards) to be tested. Two separate sets of cultures without drugs were seeded, one as control of growth to ensure that cells remained in exponential phase of growth, and another without cells as control of medium. All determinations were carried out in duplicate.

After three days of incubation at 37° C., 10% $CO_2$ in a 98% humid atmosphere, 150 µg of MTT is added to each well in 50 µl aliquots of assay medium. Plates were incubated for an additional 4 hours and 100 µl aliquots of isopropanol were added to each well. The broad absorption spectrum for the isopropanol solution of this crystal is optimal at 570 nm. Optical density values were obtained with the help of a Dynatech microplate reader and the results of the assay were used to generate graphics from which $IC_{50}$ was calculated; i.e., wherein the $IC_{50}$ is the test concentration which produces 50% cell growth inhibition.

Oother Biological Properties

The lamellarin compounds also possess immunomodulation activity, and will thus be useful as immunomodulator compounds. Immunomodulator compounds and compositions, as the name implies, are useful for modulating or regulating immunological functions in warm blooded animals. Immunomodulators may be immunostimulants for building up immunities to or initiate healing of certain diseases and disorders. Conversely, they may be immunoinhibitors or immunosuppressors for preventing undesirable immune reactions of the body to foreign materials and autoimmune diseases.

Immunomodulators have been found to be useful for treating systemic autoimmune diseases, such as lupus erythematosus, as well as immunodeficiency diseases. Further, immunomodulators may be useful for immunotherapy of cancer or to prevent rejections of foreign organs or other tissues in transplants, e.g., kidney, heart or bone marrow.

Lamellarins I, K and L all exhibit comparable and significant cytotoxicity against P388 and A549 cell lines in culture ($IC_{50} \approx 0.25$ µg/ml against each cell line). Lamellarins K and L also exhibited moderate immunomodulatory activity (LcV:MLR 147 and 98 respectively), and as such, have specific art recognized utilities related thereto.

As shown below in Table IV, the lamellarin compounds M, J and N triacetate, have surprisingly been found to have in vitro antitumor activities which are significantly better, particularly against A549 cells, than the lamellarins I, K and L.

As shown below in Table V, the in vivo antitumor activity of lamellarin K is consistent with the in vitro activity demonstrated above. Based upon these data, it is believed that the lamellarin compounds disclosed herein will be useful as antitumor compounds, particularly against the following tumor cell types; leukemia (P388), human lung carcinoma (A549), human colon carcinoma (HT-29), human melanoma (MEL-28).

TABLE IV

Lamellarin In Vitro Activity vs. Tumor Cell lines (IC$_{50}$ μg/mL)

|  | P388 | A549 | HT-29 | MEL-28 |
|---|---|---|---|---|
| Lamellarin I | 1 | 1 | 2 | — |
| Lamellarin K | 0.25 | 0.25 | 1 | — |
| Lamellarin L | 0.25 | 0.25 | 2 | — |
| Lamellarin M | 0.05 | 0.025 | 0.5 | 0.5 |
| Lamellarin J | 0.1 | 0.025 | 2.5 | 2.5 |
| Lamellarin N triacetate | 0.1 | 0.012 | 5 | 5 |

TABLE V

In Vivo Anti-Tumor Activity vs P388 Lymphocytic Leukemia

| compound | Dose (mg/kg) inject. Total | Schedule & Route | Body Weight Day 0 (gm) + SD | Body Weight Day 5 (gm) + SD | Body Weight Change (gm) Day 5 | Mean Survival Time | % T/C |
|---|---|---|---|---|---|---|---|
| LAM K (7) | 15.000 75.000 | QD 1–5 ip | 19.5 ± 0.5 | 20.7 ± 0.5 | 1.2 | 28.3 ± 5.9 | >135.0° |

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method of treating multidrug resistant tumors in mammals, comprising administering to a patient in need of such treatment, an effective MDR inhibiting amount of an anti-MDR lamellarin compound selected from the group consisting of lamellarin A, B, D-triacetate, I, I-acetate, I-methylate, J, K, K-triacetate, L, L-triacetate, M, M-triacetate, and N-triacetate or mixtures thereof.

2. The method of claim 1, wherein the lamellarin compound is lamellarin A.

3. The method of claim 1, wherein the lamellarin compound is lamellarin B.

4. The method of claim 1, wherein the lamellarin compound is lamellarin D-triacetate.

5. The method of claim 1, wherein the lamellarin compound is lamellarin I.

6. The method of claim 1, wherein the lamellarin compound is lamellarin I-acetate.

7. The method of claim 1, wherein the lamellarin compound is lamellarin I-methylate.

8. The method of claim 1, wherein the lamellarin compound is lamellarin J.

9. The method of claim 1, wherein the lamellarin compound is lamellarin K.

10. The method of claim 1, wherein the lamellarin compound is lamellarin K-triacetate.

11. The method of claim 1, wherein the lamellarin compound is lamellarin L.

12. The method of claim 1, wherein the lamellarin compound is lamellarin L-triacetate.

13. The method of claim 1, wherein the lamellarin compound is lamellarin M.

14. The method of claim 1, wherein the lamellarin compound is lamellarin M-triacetate.

15. The method of claim 1, wherein the lamellarin compound is lamellarin N-triacetate.

* * * * *